United States Patent [19]

Tolman et al.

[11] Patent Number: 5,274,122
[45] Date of Patent: Dec. 28, 1993

[54] ACIDIC DERIVATIVES OF HOMOCYSTEINE THIOLACTONE

[75] Inventors: Richard L. Tolman, Warren; Stephen Marburg, Metuchen; William J. Leanza, Berkeley Heights, all of N.J.

[73] Assignee: Merck & Co., Inc., Rahway, N.J.

[21] Appl. No.: 963,324

[22] Filed: Oct. 15, 1992

[51] Int. Cl.$^5$ .......................................... C07D 333/36
[52] U.S. Cl. ........................................ 549/6; 549/63; 549/321; 530/404
[58] Field of Search ................. 514/415, 445, 95; 549/321, 63, 6

[56] References Cited

U.S. PATENT DOCUMENTS

| | | | |
|---|---|---|---|
| 4,072,703 | 2/1978 | Blum | 558/254 |
| 4,271,147 | 1/1981 | Helting et al. | 424/92 |
| 4,411,909 | 10/1983 | Gonella | 549/63 |
| 4,690,944 | 9/1987 | Chiesi et al. | 549/63 |
| 4,691,006 | 9/1987 | Stevens | 530/324 |
| 4,695,624 | 9/1987 | Marburg | 530/345 |
| 4,762,913 | 8/1988 | Stevens | 530/345 |
| 4,767,842 | 8/1988 | Stevens | 530/324 |
| 4,902,506 | 2/1990 | Anderson et al. | 424/92 |
| 4,956,273 | 9/1990 | Kennedy et al. | 435/5 |
| 5,013,548 | 5/1991 | Haynes et al. | 424/89 |
| 5,017,688 | 5/1991 | Gilbert et al. | 530/326 |
| 5,019,387 | 5/1991 | Haynes et al. | 424/89 |

FOREIGN PATENT DOCUMENTS

| | | |
|---|---|---|
| 0311228A2 | 12/1289 | European Pat. Off. |
| 0255190A2 | 2/1986 | European Pat. Off. |
| 0306219A2 | 3/1989 | European Pat. Off. |
| 0325270A2 | 7/1989 | European Pat. Off. |
| 0328403A2 | 8/1989 | European Pat. Off. |
| 0339504A2 | 11/1989 | European Pat. Off. |
| 0402088A2 | 12/1990 | European Pat. Off. |
| 3802060A1 | 7/1989 | Fed. Rep. of Germany |
| 88/00471 | 1/1988 | PCT Int'l Appl. |
| 88/08429 | 11/1988 | PCT Int'l Appl. |
| 8808429A | 11/1988 | PCT Int'l Appl. |
| 90/03984 | 4/1990 | PCT Int'l Appl. |
| 91/05864 | 2/1991 | PCT Int'l Appl. |
| 91/05567 | 5/1991 | PCT Int'l Appl. |
| 92/07876 | 5/1992 | PCT Int'l Appl. |

OTHER PUBLICATIONS

Javaherian, et al., PNAS USA 86,6768 (1989).
Marburg, et al., JACS 108, 5282 (1986), Marburg, Ill.
Palker, et al., PNAS USA 85, 1932 (1988), Palker I.
Palker, et al., J. Immunol., 142, 3612 (1989), Palker II.
Blair, et al., J. Imm. Methods, 59:129–143 (1983).
Devash, et al., PNAS 87: 3445–3449 (1990).
Fauci PNAS 83: 9278–9283 (1986).
Goudsmit, et al., Res. Virol. 140: 419–436 (1986).
Rudinger in J. A. Parsons ed Peptide Hormones, pp. 1–7 University Park Press Baltimore (1976).

(List continued on next page.)

Primary Examiner—Richard L. Raymond
Assistant Examiner—Mary Cebulak
Attorney, Agent, or Firm—Gerard H. Bencen; Jack L. Tribble; Paul D. Matukaitis

[57] ABSTRACT

Homocysteine thiolactone derivatives in which the nitrogen is acylated with groups containing acidic functionalities have been synthesized. These include the succinyl, the carboxymethylglutaryl, the 3-phosphonopropionyl and the 3-sulfopropionyl derivatives. These thiolactones can be used to introduce a thiol functionality into proteins such as the outer membrane protein complex of *Neisseria meninioitidis* (OMPC) allowing conjugation with electrophilic ligands. This chemistry is similar to known N-acetyl-homocysteine thiolactone chemistry, but the pK$_a$ values are such that at pH 7, concomitant negative charge is introduced into the conjugate. Such negative charge neutralizes excess positive charge introduced when arginine- and lysine-rich peptides are bonded as ligands. In the case of OMPC, introduction of positive charge commonly effects irreversible precipitation of the conjugate. Conjugates prepared with the anionic thiolactones have improved solubility.

2 Claims, No Drawings

OTHER PUBLICATIONS

Emini, et al., *Nature*, vol. 20, pp. 728–730 (1992).
Matsushita, et al., J. of Virol., 62, No. 6 pp. 2107–2114 (1988).
Emini et al., J. of Virol., 64, No. 8, pp. 3674–3678 (1990).
Helting, et al., Act path. microbiol.scand. 89, pp. 69–78 (1981).
Girard, et al., Proc. Natl. Acad. Sci. USA, 88, pp. 542–546 (1991).
Biberfield & Emini, *AIDS*, 5, (Suppl. 2), pp. S129–S133 (1991).
Goudsmit, et al., *P.N.A.S.* 85: 4478–4482 (1988).
Rusche, et al., *P.N.A.S.* 85: 3198–3202 (1988).
Frasch, C. and Robbins, J., *J. Exp. Med.* 147: 629–644 (1978).
Barnes, D., *Research News* 240: 719–721 (1988).
Hilleman, M., *Vaccine* 6: 175–179 (1988).
Frasch, C. and Gotschlich, E. *J. Exp. Med.* 140: 87–104 (1974).
Putney, S., et al., Chem. Abst. 110:89579f, p. 162 (1988).
Fujii, N., et al., Int. *J. Pep. Prot. Res.* 26: 121–129 (1985).
Robertson, G. et al., *J. Virol. Meth.* 20:195–202 (1988).
Klotz, I. M. & Heiney, R. E., *J. Am. Chem. Soc.* 81:3802–3 (1959).
LaRosa, et al., *Science* 249:932–935 (1990).
Sandstrom & Kaplan, *Drugs* 34: 372–390 (1987).
Lowell, G. et al., *J. Exper. Med.* 167: 658–663 (1988).
Lowell, G. et al., *Tech. Adv. in Vaccine Dev.*, 423–432 (1988).

ACIDIC DERIVATIVES OF HOMOCYSTEINE THIOLACTONE

BACKGROUND OF THE INVENTION

The outer membrane protein complex (OMPC) of *Neisseria meninioitidis* is a very effective immunogenic carrier of polysaccharide antigens and has been approved by regulatory agencies worldwide as a vaccine component (PedvaxHIB®). OMPC is a potential immunogenic carrier for peptide antigens, especially those derived from the V3 domain of gp 120, an envelope protein of the human immunodeficiency virus. The principal neutralization determinant of this V3 domain has been extensively mapped [Emini, E. A. and Conley, A. J. (1992), The Development of an AIDS Vaccine: Progress and Perspectives, in Challenges of the 1990's. New Diseases and New Therapies: Acquired Immunodeficiency Syndrome (AIDS) (R. P. Luthy and R. G. Douglas, eds.) Hanley and Belfus, Philadelphia; 85-91 and references cited therein] and has been shown to reside in the V3 disulfide loop. Indeed, substantial antipeptide responses are observed for such OMPC-peptide conjugates. A common feature of these peptides is the presence of a Gly Pro Gly Arg (Seq. Id:1:) sequence.

These peptide conjugates were prepared by reacting an electrophilic derivative of the peptide with a thiol derivative of OMPC, which was obtained by reacting the protein with N-acetylhomocysteine thiolactone [Marburg, S., et al., J. Am. Chem. Soc. 108, 5282-5287], as outlined in Scheme 1:

Scheme 1
THIOLATION AND PEPTIDE CONJUGATION OF OMPC WITH NACETYL HOMOCYSTEINE THIOLACTONE

[Structure: N-acetyl homocysteine thiolactone with NHCOCH$_3$ group] + OMPC →

OMPC-COCHCH$_2$CH$_2$SH + X—AA$_N$ ... AA$_C$—OH →
   |
   NHCOCH$_3$
A

OMPC-COCHCH$_2$CH$_2$S—Y—AA$_N$ ... AA$_C$—OH
   |
   NHCOCH$_3$

AA$_N$ = N-terminal amino acid residue and
AA$_C$ = C-terminal amino acid residue
X = electrophilic group such as bromoacetyl or 3-(N-maleimido)propionyl)
Y = methylenecarbonyl or 3-(N-succinimid-3-yl)propionyl This thiolactone has been used to introduce a thiol functionality into small molecules and macromolecules for a variety of purposes outlined in table 1, and has been particularly useful because it unambiguously defines covalency by a 'bigeneric spacer' concept, [Marburg et al., J.A.C.S. 108, 5258-5287(1986); U.S. Pat. No. 4, 695, 624]. The bigeneric spacer technology is especially significant in production of conjugate vaccines, because hydrolysis of the conjugate allows for quantitation of specific spacer components. Thus, one commonly produced spacer is S-(carboxymethyl)homocysteine, SCMHC, while another is S-(carboxymethyl)cysteamine, SCMCA. Both of these spacer components show up in a "window" in an amino acid analysis of a hydrolyzed conjugate where no naturally occurring amino acids migrate, and are thus readily quantified. This is an important safety feature because in quantitating the SCMHC or SCMCA products, the number of epitopes appended to the carrier can be determined.

TABLE 1

Application of N-Acetyl Homocysteine Thiolactone as a thiolating agent

| Molecule type thiolated | Utility |
| --- | --- |
| aminoglycoside | protein conjugation |
| muramyl dipeptide | polysaccharide conjugation |
| HSA | drug conjugation |
| enzymes | polystyrene conjugation |
| albumin microspheres | peptide-protein conjugation |
| cell surface carbohydrate | cell surface labeling |
| lactoglobulin | increased heat stability |
| oligonucleotide | fluorescence labelling |
| amino lipid | liposome preparation |

Frequently, however, OMPC-peptide conjugate preparations using N-acetylhomocysteine thiolactone technology are characterized by very poor protein recoveries (<15%) due to irreversible precipitation of the conjugate. This hampers use of such conjugates as a vaccine material and necessitates development of a practical solution to this problem. Examination of the peptide sequences that resulted in precipitation upon conjugation revealed that all were positively charged in that they contained one or more of the basic amino acids arginine, histidine and lysine, and none of the acidic ones, such as glutamic and aspartic acids. This is in contrast to polysaccharide conjugates which are almost always acidic polymers that form anions at neutral pHs and do not suffer the precipitation problems observed with the peptide conjugates (see U.S. Pat. No. 4, 695, 624).

The present invention provides acylated derivatives of homocysteine thiolactone incorporating acidic functionalities. Use of these novel compounds in lieu of the N-acetyl derivative in the conjugation generates linking molecules which impart one to two negative charges per ligand in the conjugate at neutral pHs.

Klotz, I. M. and Heiney, R. E. [J. Am. Chem. Soc. 81, 3802-3803, (1959)]reported the use of S-acetylmercaptosuccinic anhydride to thiolate proteins. However, the product of that work did not result in production of an easily quantifiable spacer (mercaptosuccinyl), and only introduced a single negative charge.

Use of the novel compounds of the instant invention in conjugate formation has been found to ameliorate the problems of conjugate insolubility, particularly when cationic ligands are used, while at the same time providing easily quantifiable linker degradation products.

SUMMARY OF THE INVENTION

Anionic homocysteine thiolactone derivatives, in which the nitrogen is acylated with groups containing acidic functionalities, have been synthesized. These include the succinyl, the carboxymethylglutaryl, the 3-phosphonopropionyl and the 3-sulfopropionyl derivatives. These thiolactones can be used to introduce a thiol functionality into proteins such as the outer membrane protein complex of *Neisseria meninigitidis* (OMPC) allowing conjugation with electrophilic ligands. This chemistry is the same as with N-acetylhomocysteine thiolactone but the pK$_a$ values are such

THIOLATION AND PEPTIDE CONJUGATION OF OMPC USING THE NEW COMPOUNDS OF THIS INVENTION

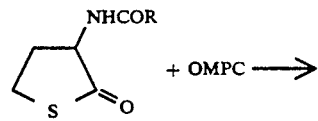 + OMPC ⟶

DETAILED DESCRIPTION OF THE INVENTION

The syntheses of the various anionic thiolactones, shown in Scheme 2, were effected either by direct acylation of homocysteine thiolactone, 2, or by conversion to the bromopropionyl derivative, 5, followed by displacement of the bromine with the appropriate nucleophiles. The preparation of the phosphonic acid, 7, proceeded via the phosphono dimethyl ester, 6, which was demethylated with trimethylsilyl bromide:

Scheme 2
SYNTHESIS OF ANIONIC THIOLACTONES

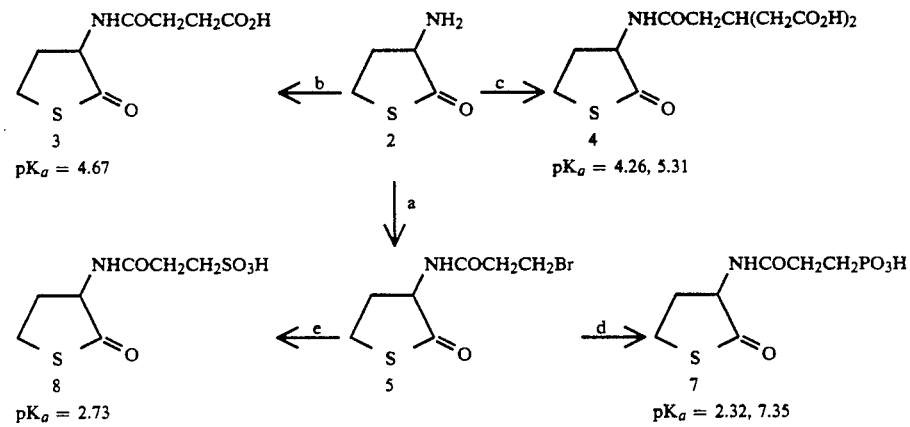

Reagents:
(a) bromopropionyl chloride;
(b) succinic anhydride;
(c) carboxymethylglutaric anhydride;
(d) trimethyl phosphite then trimethylsilyl bromide;
(e) sodium bisulfite.

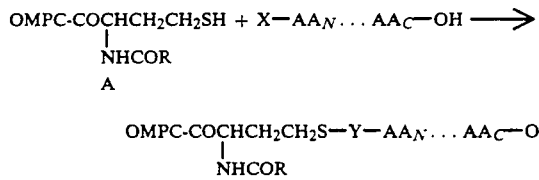

```
OMPC-COCHCH2CH2SH + X—AA_N ... AA_C—OH ⟶
       |
       NHCOR
       A

OMPC-COCHCH2CH2S—Y—AA_N ... AA_C—OH
       |
       NHCOR
```

$AA_N$ = N-terminal amino acid residue of a peptide and
$AA_C$ = C-terminal amino acid residue of a peptide
X = electrophilic group such as bromoacetyl or 3-(N-maleimido)propionyl
Y = methylenecarbonyl or 3-(N-succinimid-3-yl)propionyl
R = —CH2CH2CO2H, —CH2CH2SO3H, —CH2CH(CH2CO2H)2, —CH2CH2PO3H, —CH2C(CH3)(CH2CO2H)2

Negative charge contributed by the "R" portion of—COCH(NHCOR)CH2CH2S—Y— neutralizes excess positive charge introduced when arginine- and lysine-rich peptides are bonded as ligands. In the case of OMPC, conjugation to positively charged peptides commonly effects irreversible precipitation of the conjugate. This is particularly true with many of the human immunodeficiency virus (HIV) principal neutralizing determinant peptides (PND peptides) which are generally cationic. Conjugates prepared with the anionic thiolactones have improved solubility and are more available for vaccine formulation.

The compounds of this invention have the general formula:

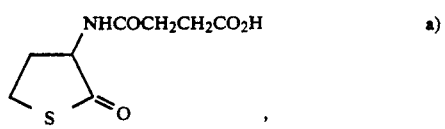

and salts thereof, wherein:
i) X is:
(a) —PO3=,
(b) —SO3—, or
(c) —CO2H; and
Y and R' are hydrogen; or
ii) both X and Y are —CH2CO2H, and R' is hydrogen or methyl; or
iii) X is —CO2H and Y is —CH2CO2H, and R' is hydrogen. Salts include alkali metal salts.

Accordingly, all of the following compounds come within the instant invention:

a)

[structure with NHCOCH2CH2CO2H]

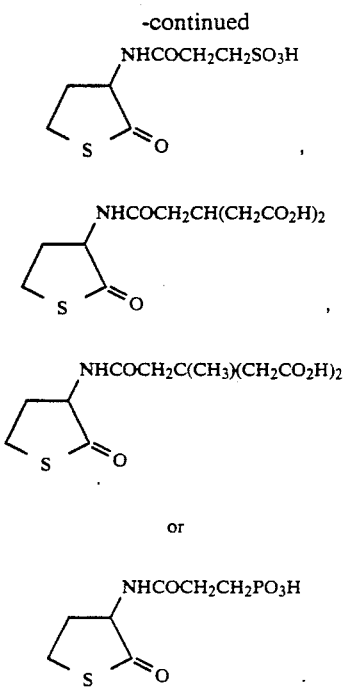

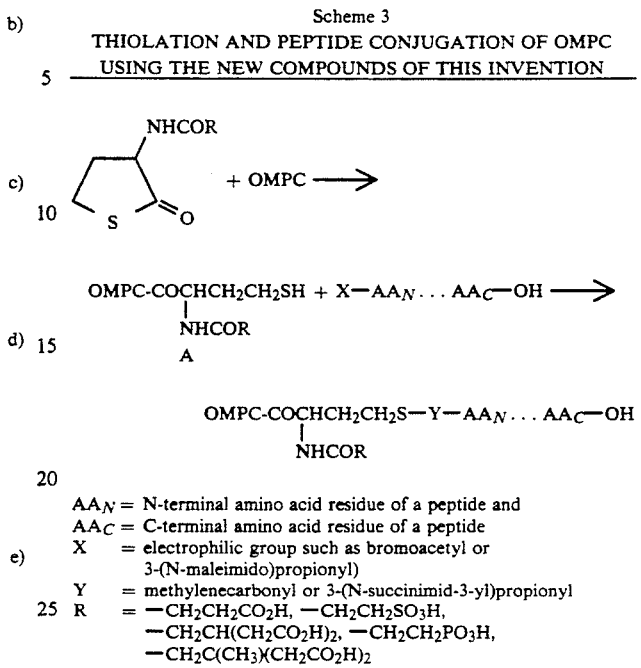

The role of a homocysteine thiolactone in the conjugation chemistry of OMPC involves acylation of the amino groups of OMPC to append a thiol group to the protein. This thiol group is then alkylated by an electrophile, such as a bromoacetyl group, which is incorporated into the molecule (i.e. peptide) to be conjugated. This is outlined in Scheme 1 (above).

The stable thioether formed in the process not only affords the covalent bond between the ligand (peptide) but also in appropriate cases allows the degree of ligand binding to be evaluated by analysis of the newly-formed amino acid, S-Carboxymethylhomocysteine thiolactone. Other electrophiles such as malemidated peptide epitopes may also be used to alkylate the thiolated proteins of this invention in which case the degree of conjugation is measured by assay of a "marker" amino acid such as b-alanine or norleucine.

Since HIV peptides were available in limited quantities and express a variety of characteristics (e.g. hydrophobic groups) which could affect the solubility of the product, bromoacetyl triarginine was chosen as a model peptide for the initial experiments. With more complex peptide ligands the effect of the anionic spacers may be less predictable. However the availability of these anionic thiolactones for use as a linking molecule offers the possibility of changing the physical properties of the varied types of macromolecules listed in table 1, affording fruitful conjugations and usable materials. Thus, the new compounds of this invention may be utilized in conjugate preparation as summarized in Scheme 3:

Conjugate immunogen, prepared by using the anionic thiolactones of this invention to covalently link peptidyl epitopes and immunogenic carrier proteins, are useful to induce immune responses to a mammal against the peptidyl epitope. Immunologically effective amounts of the conjugate immunogen should be administered intramuscularly, subcutaneously, intravenously, intraperitoneally, or by any other route found to be efficacious in achieving exposure of the immunogen to the immune responsive system.

By intramuscular administration, a does of immunogen of about 0.1 μg to about 10 mg per kilogram, and preferably about 10 μg–500 μg per kilogram of immunogen is administered, in a pharmaceutically acceptable medium. An adjuvent such as Freunds complete or incomplete, or the Ribi adjuvant may be admixed with the conjugate immunogen prior to administration. It is also beneficial to adsorb the immunogen to aluminum hydroxide gel prior to administration. Furthermore, antivirals, immunomodulators, antibacterials or other pharmaceuticals may be co-administered to advantage.

In a preferred method of using the anionic thiolactones of this invention, an HIV principal neutralizing determinant is administered as a conjugate with the OMPC of *Neisseria meninoitidis* b. The conjugate is administered intramuscularly at a dose of about 10 μg/kilogram, adsorbed to about 500 μg/ml of aluminum hydroxide at a concentration of about 300 μg/ml conjugate, or a total dose of about 300 μg of the adsorbed conjugate is administered.

Accordingly, the following conjugates were prepared and found to be nicely soluble whereas similar conjugates prepared using neutral linkages were less soluble (note: Acap is 6-aminocaproic acid) Seq ID:

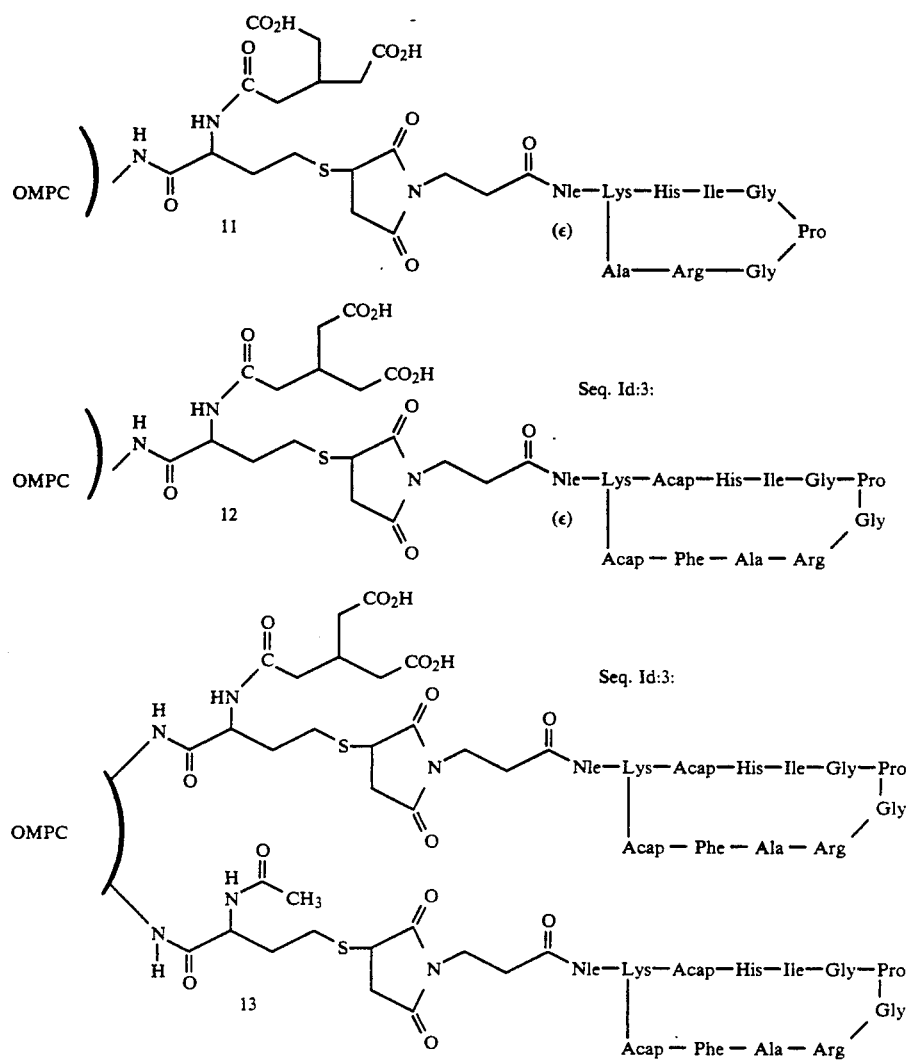

Conjugates of HIV PND peptides prepared with the anionic thiolactones of this invention raise HIV neutralizing immune response in rabbits.

Specific experiments follow which demonstrate the preparation and utility of the anionic thiolactone compounds of the instant invention. These examples are intended merely to be suggestive and should not be construed as being the only manner in which the instant compounds may be prepared or used. In the examples that follow, all manipulations of thiolated OMPC were carried out in a nitrogen purged dry-box. The nitrogen was sterilized by passage through a 0.2 μm (Gelman Acro 50) filter. An effort was made to keep reagents and equipment sterile. All centrifugations unless otherwise noted were performed in a Beckman L-80 Optima centrifuge using a 80 Ti rotor and 10 mL polycarbonate tubes. All centrifugations were effected at 43, 000 rpm, for 2 h at 4° C. unless otherwise noted. Amino acid analyses were done on a Beckman 6300 amino acid analyzer. NMR spectra were obtained on Varian 300 MHz and 400 MHz instruments. The protein titers were determined by the method of Lowry [Lowry, O. H., Rosebrough, N. J., Farr, A. L. and Randall, R. J. (1951) J. Biol. Chem. 193, 265-275] using a Zymate II robotic system; thiol titers were determined by the method of Ellman [Ellman, G. L. (1959), Arch. Biochem. Biophys. 82, 70-77]; pKa values were determined by titration. Numbers referring to compounds refer to the foregoing figures. Note that the anionic thiolactones are enantiomers at the 2-position and are used as racemic materials.

EXAMPLE 1

D, L-N-Succinylhomocysteine thiolactone, NSUTL (3)

D, L-Homocysteine thiolactone hydrochloride, 2, (1.84 g, 12 mmol) was suspended in 20 mL of DMF and to it was added 1.04 g (10 mmol) of succinic anhydride and 1.79 mL of N, N-diisopropylethylamine (DIEA) (10 mmol). The mixture was stirred at room temperature for 1 h after which an additional 0.9 mL of DIEA (0.5 mmol) was added. Stirring was continued for another 45 min after which a third charge of DIEA (0.9 ml, 5 mmol) was added. After stirring for an additional 2 h at room temperature the mixture was stored at 4° C. overnight. It was then quenched onto 22 g of ice (pH=7.1) and the solution applied to a 30 mL column of Dowex 1 (acetate form). This was washed free of thiolactone and then eluted with 2M formic acid. The uv positive fractions were concentrated to 2.13 g of N-succinylhomocysteine thiolactone, mp 128°-135° C. FAB MS showed the major peak at m/z 218 (MH+). A small amount (47 mg) of this material was recrystallized by dissolving in acetonitrile, filtering and precipitating crystals with equal volumes of chloroform and cyclohexane affording pure product, mp 140°–142° C. $^1$HNMR (CDCl$_3$) δ4.67 (dd, 1H, J=7.0, 12.7), 3.44 (dt, 1H, J=5.4, 11.5), 3.33 (ddd, 1H, J=1 2, 7.1, 11.5), 2.55–2.7 (m, 5H), 2.20 (dq, 1H, J=7.1, 12.2). Anal. Calcd for C$_8$H$_{11}$NO$_4$S: C, 44.24; H, 5.07; N, 6.45; S, 14.75. Found: C, 44.17; H, 5.04; N, 6.43; S, 4.48.

EXAMPLE 2

N-(3-Carboxymethylglutaryl)-homocysteine thiolactone, CMGTL (4)

A mixture of carboxymethylglutaric an (1.72 g, 10 mmol) and homocysteine thiolactone hydrochloride, (1.85 g, 12 mmol) in dry DMF (10 mL) was stirred in a flask capped with a septum, cooled in an ice bath and DIEA (4.3 mL, 25 mmol) was added via syringe through the septum over a period of 15 min. After ageing the mixture for 2 hr, a stream of nitrogen was passed through the solution for 15 min to remove excess amine and then 15 g of ice was added. The pH at this point was 7. The solution was applied to a column of Dowex 1, (acetate form, 80 mL) which was eluted with water (250 mL) followed by 2N formic acid (350 mL). The acidic fraction was concentrated to 20 mL and applied to a column of neutral polystyrene resin (80 mL of HP-20, Pharmacia Fine Chemicals) and washed with 150 mL water. The product was recovered by elution with 250 mL of 12% acetonitrile -water and lyophilized. This afforded 2.2 g of a material which was crystallized from acetonitrile-water affording 1.9 g of 4, mp. 149°–150° C. MS (FAB) m/z 290 [MH+]. $^1$HNMR (D$_2$O) δ4.68 (dd, .1H, J=7.0, 12.8), 3.45 (dt, 1H, J=5.5, 11.4), 3.35 (ddd, 1H J=1.3, 7.0, 11.4), 2.71 (m, 1H, J=7.0), 2.62 (m, 1H) 2.52 (dABq, 2H), 2.50 (d, 2H, J=7.0), 2.43 (dABq, 2H), 2.22 (dq, 1H, J=7.0, 12.8). Anal. Calcd for C$_{11}$H$_{15}$NO$_6$: C, 45.67; H, 5.23; N, 4.84; S, 11.08. Found: C, 45.64; H, 5.34, N, 5.05; S, 11.28.

EXAMPLE 3

D, L-N-(3-Bromopropionyl) homocysteine thiolactone (5)

D, L Homocysteine thiolactone hydrochloride, 2, (52.0 g, 0.34 mol) was dissolved in 135 mL of water and covered with 300 mL of ethyl acetate. While stirring at 0° C., 39 mL of 3-bromopropionyl chloride (0.78 mol) was added in 2 mL aliquots alternately with 20 mL aliquots of 2.5 N sodium hydroxide maintaining the pH at 7.35. After ageing at room temperature for 1 h without stirring a yellow precipitate (76 g) was filtered. This precipitate was dissolved in 600 mL of refluxing ethyl acetate and filtered, hot, through Celite. After 72 h at 4° C. compound 5, (40.5 g, 0.16 mol) was obtained. The supernatant fluid was reduced to 200 mL and seeded. After 18 h at 4° C. an additional 9.6 g was obtained. A total of 50.1 g of compound 5 was isolated (58% yield): mp 142.5°–149.1° C. $^1$HNMR (CDCl$_3$) δ6.06 (s, 1H), 4.51 (pentet, 1H, J=8.4), 3.6 (m, 2H), 3.36 (dt, 1H, J=6.8, 15), 3.26 (dd, 1H, J=8.8, 15), 2.98 (m, 1H), 2.81 (m, 2H), 1.94 (dq, 1H, J=9.2, 16.6). Anal. Calcd for C$_7$H$_{10}$NO$_2$SBr: C, 33.34; H, 4.01; N, 5.56; S, 12.72; Br, 31.69. Found: C, 33.60; H, 3.88; N, 5.51; S, 12.86; Br, 31.78.

EXAMPLE 4

D, L-N-(3-Dimethylphosphonopropionyl) homocysteine thiolactone (6)

D, L -N-(3-Bromopropionyl)homocysteine thiolactone, 2, (5 g, 19.8 mmol) was covered with 60 mL of trimethylphosphite. This solution, with nitrogen bubbling through it, was refluxed at 119° C. for 7 h. The excess trimethylphosphite was removed by distillation at 48° C. under vacuum leaving a clear yellow oil. Ethyl ether was slowly added to the oil with vigorous stirring to produce a white precipitate (5.7 g). The precipitate was recrystallized by dissolving it in 200 mL of boiling toluene, and adding hexane to the cloud point. White crystals, compound 6, (3.4 g, 61%) were filtered after ageing 72 h at 4° C.; mp 109.5°–111.5° C.; $^1$HNMR (CDCl$_3$) δ6.5 (s, 1H), 4.50 (pentet, 1H, J=6.5), 3.72 (2d, 6H), 3.33 (dt, 1H, J=5.1, 11.5), 3.24 (ddd, 1H, J=1.3, 7.0, 11.5), 1.86 (m, 1H), 2.53 (m, 2H), 2.1 (dt, 2H, J=7.75, 17.86), 1.95 (dq, 1H, J=7.1, 12.4). Anal. Calcd for C$_9$H$_{16}$NPO$_5$S: C, 38.43; H, 5.74; N, 4.98; P, 11.01; S, 11.40. Found: C, 38.31; H, 5.59; N, 4.90; P, 11.24; S, 11.30.

EXAMPLE 5

D, L-N-(3-Phosphonopropionyl)homocysteine thiolactone, NPHTL D, L-N-(7)

D, L-N-(3-Dimethylphosphonopropionyl) homocysteine thiolactone, 6, (1.0 g, 3.6 mmol) was dissolved in 18 mL of dichloromethane, bromotrimethylsilane (7.5 mL, 56.8 mmol) added and the reaction aged at 25° C. for 16 h. The solvent and volatiles were removed with a stream of N$_2$, 100 mL of methanol added, and the solution aged at 25° C. for 2 h. The methanol was then removed in vacuo. The remaining orange oil was dissolved in 8 mL of water, charged to 7 mL of Dowex 1X8 (200–400 mesh, acetate form), and the column then washed with 250 mL of water. Compound 7 was eluted with 200 mL of 2 N formic acid. Complete removal of formic acid under reduced pressure gave a clear oil (0.78 g, 3.1 mmol, 87% yield) which crystallized after 24 h at 25° C. $^1$HNMR (D$_2$O) δ4.71 (dd, 1H, J=7.1, 12.6), 3.47 (dt, 1H, J=5.4, 11.5), 3.36 (dd, 1H, J=7.1, 11.5), 2.54–2.68 (m, 3H), 2.23 (dq, 1H, J=7.1, 12.6), 2.06 (dt, 2H, J=8.7, 17.4). MS (FAB) m/z 252 (MH+). Anal Calcd for C$_7$H$_{12}$NPO$_5$S.0.25H$_2$O: C, 32.62; H, 4.89; N, 5.44; P, 12.02; S, 12.44. Found: C, 32.59; H, 4.81; N, 5.43; P, 12.03; S, 12.33.

EXAMPLE 6

N-(3-Sulfopropionyl)homocysteine thiolactone sodium salt, NSFTL (8)

A Solution of N-(3-Bromopropionyl) homocysteine thiolactone, 5, (1.0 g, 3.9 mmol) in DMF (6 mL) was added dropwise to a solution of sodium bisulfite (1.25 g, 12 mmol) in 16 mL of a 3:1 H$_2$O: DMF mixture. The pH was adjusted to 8.8 by the addition of DIEA (1.5 mL), and the milky suspension stirred at room temperature for 18 hr. The mixture was filtered to remove undissolved sodium sulfite and the filtrate evaporated in vacuo to a solid. This was redissolved in 10 mL of water and charged to a 60 mL column of Dowex 50×4 (H+ form) and eluted with 125 mL of water. The eluate was evaporated to 5 mL, adjusted to pH 7.2 with 5 N NaOH and applied to a column of brominated polystyrene resin (90 mL, SP-207, Mitsubishi Chem. Co.). The column was eluted with water and after a forerun of 90 mL (AgNO₃ positive), 200 mL (uv positive) was collected and evaporated to dryness. The solid was dissolved in 15 mL of water and the product precipitated by the slow addition of 15 mL of absolute ethanol yielding 0.6 g (54%) of an amorphous white solid. ¹HNMR (D₂O) δ4.70 (dd, 1H, J=7, 12.5), 3.46 (dt, 2H, J=5.5, 11.7), 3.36 (ddd, 1H, J=1.4, 7.0, 11.7), 3.19 (m, 2H), 2.74 (m, 2H), 2.64(dddd, 1H, J=1.4, 5.5, 7.0, 12.5), 2.22 (dq, 1H, J=7, 12.5). Anal. (dried 80° C./4 hr) Calcd for $C_7H_{10}NO_5S_2$.Na: C, 30.54; H, 3.66; N, 5.09; S, 23.29. Found: C, 30, 28; H, 3.54; N, 4.98; S, 23.54.

EXAMPLE 7

N-(3-carboxymethyl-3-methyl-glutaryl)-Homocysteine Thiolactone, MCMGTL:

Following the procedure in Example 2, Homocysteine Thiolactone Hydrochloride, 1.85 g (12 mmol) is acylated with 3-carboxymethyl-3-methyl-glutaric anhydride, 1.86 g (10 mmol) in the presence of diisopropylethylamine, 4.3 ml (25 mmol) in 10 ml of dry DMF. The product, MCMGTL, is purified by chromatography on Dowex 1 (acetate form) resin followed by chromatography on neutral polystyrene resin (HP-20) and is isolated by evaporation of the appropriate eluate.

EXAMPLE 8

N-Tricarballylyl-homocysteine thiolactone. NTCTL

Following the procedure in example 2, the reaction of homocysteine thiolactone (184 mg) with tricarballylic anhydride (158 mg) and diisopropylethylamine (522 mL) gave N-tricarballylyl -homocysteine thiolactone as an amorphous mixture of isomers.

EXAMPLE 9

N-a-Bromoacetyl-L-arginyl-L-arginyl-L-arginine (10)

Resin bound triarginine which was tris-guanidino protected by 4-methoxy-2, 3, 6-trimethylbenzenesulfonyl (Mtr) groups was synthesized on a 0.180 mmole scale on a Milligen Model 9050 peptide synthesizer. Preloaded Fmoc-Arg(Mtr)-OPKA resin (Milligen Co.) was coupled with Fmoc-Arg(Mtr) pentafluorophenyl esters using single 60 min reactions and a piperidine deprotection. The final resin was rinsed with methylene chloride and ether and dried in vacuo. A Kaiser test was positive for amine. This resin with the bound tripeptide derivative was swollen in 7 mL of N-methylpyrrolidine (NMP) and then 31 μL of DIEA and 85 mg of p-nitrophenyl bromoacetate added. The resin was agitated at RT until a negative Kaiser test was observed. The bromoacetylated peptidyl resin was then washed with DMF (50 mL), methylene chloride (50 mL) and ether (50 mL). Cleavage from the resin was effected by TFA (20 mL) containing 3% thioanisole for 7 h at RT. The resin was removed by filtration, washed with TFA (3×20 mL) and the combined filtrates concentrated in vacuo. The residue was triturated with ether affording crude product (82 mg) which was purified by HPLC (Waters RCM 25×10 Delta Pack C₁₈, 10 mL/min, using a gradient [8% to 15% acetonitrile (0.1% TFA) in 20 min] affording 14.6 mg of N_a-bromoacetyl-L-arginyl-L-arginyl-L-arginine. FAB MS m/z 607 (MH+).

EXAMPLE 10

Thiolation of OMPC with N-Succinylhomocysteine thiolactone and reaction with Bromoacetyltriaroinine 5 ml of OMPC (6 mg/ml) was ultracentrifuged at 43,000 rpm, 4° C. for two hours. The OMPC pellet was resuspended using a DOUNCE homogenizer, in 8 ml of thiolating solution (85 mg EDTA, 17 mg DTT, and 120 mg of N-succinyl-homocysteine thiolactone in 10 ml of 0.1M, pH 11 borate buffer).The thiolation was allowed to proceed at room temperature for 18 hours under N₂, and the solution was then centrifuged at 43, 000 rpm, 4° C. for two hours. The pellet was resuspended in 10 ml of 0.1M pH 8 phosphate buffer, recentrifuged, and resuspended in 5 ml of pH 8 buffer . An Ellmans assay indicated a sulfhydryl titer of 0.64 μmoles/mL. To 4 ml of this suspension was added bromoacetyl triarginine (9 mg) and the mixture was aged at room temperature overnight. The mixture was centrifuged at 3000 rpm for two minutes and the supernatant sampled for analysis. The protein content (Lowry) was 1.1 mg/mL.

EXAMPLE 11

Thiolation of OMPC with Phosphonopropionyl-homocysteine thiolactone and reaction with bromoacetyl triarginine Following the procedure in example 10, OMPC(5 mL, 3.8 mg/mL) was thiolated with phosphonopropionylhomocysteine thiolactone , and the resulting thiolated OMPC (SH titer, 334 nM/mL) reacted with bromoacetyltriarginine providing a conjugate having 1.38 mg/mL protein and a SCMHC content of 63 nM/mL.

EXAMPLE 12

Thiolation of OMPC with Carboxymethylglutarylhomocysteine thiolactone and reaction with Bromoacetyltriarginine OMPC was thiolated with CMGTL as in Example 10 and was found to have an Ellmans titer of 275 nM SH/ml. 1 ml of this suspension was added to a vial containing 1.5 mg of bromoacetyl triarginine. The mixture was kept in the refrigerator overnight then centrifuged for 3 minutes at 3000 rpm and the supernatant sent for Lowry and aminoacid analyses. Lowry=3.1 mg/ml; S-Carboxymethyl homocysteine=193 nM/ml. When Bromoacetyl triarginine was added to OPMC which was thiolated with the neutral reagent, N-Acetyl Homocysteine Thiolactone (Ellmans assay=399 nM SH/ml) and the reaction worked up as above, the Lowry assay was only 0.9 mg/ml.

EXAMPLE 13

Preparation of cPND724 (Seq. ID: 4:):

The linear peptide (Seq. Id:4:)

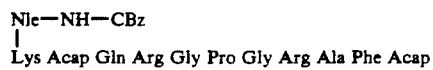

was synthesized using Fmoc-Lys(e Nle)-OH, Fmoc chemistry and single coupling on an ABI-431 solid phase synthesizer, at 0.25 mmolar scale (Acap stands for 6-aminocaproic acid). The peptide was cleaved from the resin with trifluoroacetic acid (TFA) and anisole, 20° C., 4.5 hours. About 0.4 g of crude material was purified on a Waters Delta Prep system, and the peak fraction was dried. Mass spectrometry analysis gave a molecular weight of 1473, which is consistent with the calculated molecular mass.

The linear peptide (0.34 g, 0.22 mmol) was dissolved in 200 mL DMF, along with diisopropylethylamine (DIEA) (0.12 mL, 0.66 mmol), BOP (111 mg, 0.25 mmol), and HOBt (38 mg, 0.25 mmol). An additional aliquot of BOP (100 mg, 0.25 mmol) was added after analysis of an aliquot revealed the presence of residual linear peptide. After reacting for 18 hours at room temperature, a 1 mL aliquot was evaporated, redissolved in 50% acetic acid, and analyzed by HPLC. All of the linear material was converted to cyclic peptide according to this analysis. Therefore, the entire reaction was dried, redissolved in 50% acetic acid, and purified by HPLC. The sample was loaded on a $C_{18}$ column equilibrated with aq. 0.1% TFA, and the peptide eluted over 60 minutes by gradient up to 80% $CH_3CN$/0.1% TFA.

Peak HPLC fractions were combined, dried, redissolved in aq. alcohol and hydrogenated over a palladium catalyst. The catalyst was filtered off and the sample was dried, and then dissolved in 50% acetic acid. The sample was repurified by HPLC, and peak fractions eluting over 70 minutes in an aq. 0.1% TFA-70% $CH_3CN$/0.1% TFA gradient were pooled and dried. Mass spectroscopic analysis gave a molecular weight of 1336, which is consistent with the calculated mass for cPND724.

EXAMPLES 14-15

Preparation of cPND955 (Seq. Id:3:). and cPND815 (Seq. Id:2:)

Using essentially the same procedure as in Example 13, but varying the primary amino acid sequence the following compounds were prepared, and the molecular weight confirmed by mass spectroscopic analysis.

40% MeCN in 0.1% TFA over 30 minutes. The peak eluting between 21.6-30.6 minutes was collected, concentrated and lyophilized. Wt 9.3 mg.; FAB-MS, m/z 1454, M+H.

EXAMPLE 17

Preparation of Maleimido Propionyl cPND815. MPP-cPND815(Seq. Id:2:)

To a solution of cPND815 (12 mg) in 1 ml of 2:1 MeCN/$H_2O$ was added sodium bicarbonate, (260 ul of 0.2M) and Maleimido Propionyloxy Succinimide (5 mg). The mixture was stirred in ice for 50 min then quenched with 4 μl. of TFA. The maleimido peptide was isolated by preparative HPLC (isocratic with 24% MeCN in 0.1% TFA for 10 minutes, then with a gradient of 24-34% for 10 minutes). The peak eluting between 16 to 24 minutes was concentrated and lyophilized providing MPP-cPND815 as a white powder. Wt. 10 mg; FAB-MS, m/z 1081, M+H.

EXAMPLE 18

Thiolation of OMPC with CMGTL and reaction with Maleimido Propionyl Peptide-cPND815. (Seq. Id:2:)

OMPC (9 ml of 3.2 mg/ml) was ultracentrifuged at 43K, for 2 hrs. and the resulting pellet was resuspended in 8 mL of a solution of 78 mg CMGTL, 85 mg of EDTA and 18 mg of DTT in 10 ml of pH 11, 0.01 M Borate buffer. The suspension was flushed with nitrogen and kept at room temperature for two days, then ultracentrifuged and the pellet resuspended in 10 mL of 0.1M pH7 phosphate buffer. This was ultracentrifuged and the pellet finally suspended in 7.6 ml of 0.1M pH 8 phosphate buffer. (Ellmans=0.387 μM SH/ml.) To 5.5 mL of this suspension was added 625 μL of a solution containing 3.39 μM/ml of Maleimido Propionyl cPND815 (ca. 10 mg in 1.5 ml water). After 15 min an Ellmans titer for residual SH groups was negative. The suspension was dialyzed vs 4 L. of 0.1M pH8 phosphate overnight. (Lowry protein=2.16 mg/ml; Spinco NLe=175 nM/ml corresponding to a peptide loading of 7.5%). This conjugate was aqueous soluble. By contrast, the reaction of Maleimido Propionyl CPND815 with OMPC thiolated with the neutral reagent N-

| Peptide | Structure | Mass | EX # | Seq. Id |
|---|---|---|---|---|
| cPND955 | Nle-NH2<br>ε \|<br>Lys—Acap—His—Ile—Gly—Pro—Gly—Arg—Ala—Phe—Acap<br>└──────────────────────────────────────────┘ | 1302 | 14 | 2 |
| cPND815 | Nle-NH2<br>ε \|<br>Lys—His—Ile—Gly—Pro—Gly—Arg—Ala<br>└──────────────────────────────┘ | 929 | 15 | 2 |

EXAMPLE 16

Preparation of maleimido propionyl cPND955 (Seq. Id:3:)

To a cooled solution of cPND955 triflouroactate salt, (9.5 mg, in 0.8 ml of 70% acetonitrile) was added 61 μl. of 0.5M sodium bicarbonate solution followed by 2.3 mg. of maleimidopropionyl (N-Hydroxy) succinimide. The solution was stirred in ice for 1 hr. and the course of the reaction was followed by reverse phase HPLC (30% MeCN/0 1% TFA). The reaction was quenched with 2.3 μl of TFA and the peptide was isolated by preparative HPLC using gradient elution from 20 to Acetylhomcysteine thioactone resulted in almost complete precipitation. The supernatant from this reaction gave a Lowry protein assay of 0.12 mg/ml.

EXAMPLE 19

Conjugation of CMGTL-OMPC with MPP-cPND955 (Seq. Id:3:):

OMPC was thiolated with CMGTL as in Example 18 and was found to have an Ellmans titer of 0.361 μM SH/mL. To 5 mL of this suspension was added 0.65 mL of a solution (3.1 μM/ml) of MPP-cPND955. The reaction mixture was dialyzed vs 4 L of 0.01M, pH7 phosphate buffer overnight at 4° C. and then removed to a graduated tube: Vol. 5.8 ml, Lowry protein=2.84 mg/ml, Amino Acid Analysis Nle=219 nM/ml, Peptide loading=10%. This conjugate was nicely aqueous soluble.

EXAMPLE 20

Thiolation of OMPC with MCMGTL and reaction with MPP-cPND955. (Seq. Id:3:):

Following the procedure of Example 18, OMPC is thiolated with N-(Carboxymethyl-3-methylglutaryl)-Homocysteine thiolactone and then reacted with Maleimido Propionyl cPND 955 affording an OMPC-MPP cPND 955 conjugate containing a 3-carboxymethyl-3 methylglutary substituted spacer.

EXAMPLE 21

Thiolation of OMPC with CMGTL and N-Acetyl-Homocysteine Thiolactone and conjugation to MPP-cPND 955. (Seq. Id:3:):

OMPC (5ml of 4.3 mg/ml) was ultracentrifuged at 43K for 2 hr and the pellet was resuspended in 5 ml of a solution of 86 mg CMGTL, 85 mg of EDTA, and 17 mg of DTT in 10 ml of pH 11, 0.1 M borate buffer. The suspension was flushed with nitrogen and kept overnight at room temperature. Sodium Hydroxide, (100 μl of 5 N) and N-Acetyl Homocysteine Thiolactone Hydrochloride, 40 mg, were added and the mixture was tumbled overnight. The suspension was diluted with 0.1M, pH 7 phosphate buffer (4 ml), ultracentrifuged, and the pellet resuspended in 7 ml of pH 7 buffer. The suspension was again ultracentrifuged and the pellet resuspended in 4.2 ml of pH 8, 0.1 M TED buffer, (Ellmans=0.75 μM SH/ml). To 3 ml of this suspension was added MPP-cPND955, (1.2 ml of 2 μM/ml). After 1 hr. the suspension was dialyzed overnight at 4° C. vs 4 l of pH 8. 0.01 M phosphate buffer. The final dialysate volume was 4.6 ml; Lowry protein=1.94 mg/ml, Amino Acid Analysis Nle=387 nM/ml, Peptide loading=29%.

EXAMPLE 22

Conjugation of CMGTL-OMPC with MPP-cPND955 (Seq. Id:3:) and MPP-cPND815 (Seq. Id:2:):

Following the procedure of examples 18, OMPC is thiolated with CMGTL and then reacted with about an equimolar amount of MPP-cPND955 and MPP-cPND815 to form a conjugate having different peptidyl epitopes.

EXAMPLE 23

Thiolation of OMPC with NSUTL, MCMGTL, NTCTL, or NSHTL, and conjugation with MPP-cPND955 (Seq. Id:3:), MPP-cPND815 (Seq. Id:2:), or MPP-cPND955 and MPP-cPND815

Using NSUTL, NTCTL, MCMGTL, or NSHTL, OMPC is thiolated following the procedure of example 19 and is then reacted with MPP-cPND955, MPP-cPND815, or MPP-cPND955 and MPP-cPND815, according to examples 18, 19 or 22 respectively.

---

What is claimed is:
1. A compound of formula:

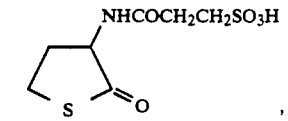

and salts thereof wherein
i) X is:
  (a) —PO$_3$= and
  (b) —SO$_3$—; and Y and R' are hydrogen; or
ii) both X and Y are —CH$_2$CO$_2$H, and R' is hydrogen or methyl; or
iii) X is —CO$_2$H, and R' is hydrogen.
2. A compound having the formula:

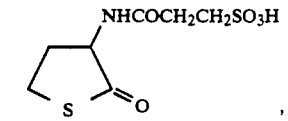
a)

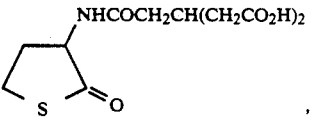
b)

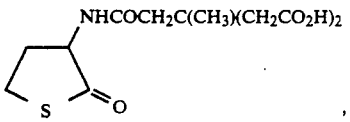
c)

or

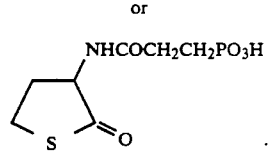
d)

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: both ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:1:

Gly Pro Gly Arg
    1

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: internal ( i x ) FEATURE:

( A ) NAME/KEY: Modified-site
          ( B ) LOCATION: 1
          ( D ) OTHER INFORMATION: /label=Nle
                  / note="norleucine"

( i x ) FEATURE:
          ( A ) NAME/KEY: Cross-links
          ( B ) LOCATION: 2..9
          ( D ) OTHER INFORMATION: /label=cycle
                  / note="amide bond through Lys epsilon amino"

( x i ) SEQUENCE DESCRIPTION: SEQ ID NO:2:

Leu Lys His Ile Gly Pro Gly Arg Ala
    1               5

( 2 ) INFORMATION FOR SEQ ID NO:3:

( i ) SEQUENCE CHARACTERISTICS:
          ( A ) LENGTH: 12 amino acids
          ( B ) TYPE: amino acid
          ( D ) TOPOLOGY: both ( i i ) MOLECULE TYPE: peptide ( i i i ) HYPOTHETICAL: NO ( v ) FRAGMENT TYPE: internal ( i x ) FEATURE:
          ( A ) NAME/KEY: Modified-site
          ( B ) LOCATION: 1
          ( D ) OTHER INFORMATION: /label=Nle
                  / note="norleucine"

( i x ) FEATURE:
          ( A ) NAME/KEY: Cross-links
          ( B ) LOCATION: 2..12
          ( D ) OTHER INFORMATION: /label=cycle
                  / note="amide bond through Lys alpha amino"

( i x ) FEATURE:
          ( A ) NAME/KEY: Modified-site
          ( B ) LOCATION: 3
          ( D ) OTHER INFORMATION: /label=Acap
                  / note="6-aminocaproic acid"

( i x ) FEATURE:
          ( A ) NAME/KEY: Modified-site
          ( B ) LOCATION: 12
          ( D ) OTHER INFORMATION: /label=Acap
                  / note="6-aminocaproic acid"

( x i ) SEQUENCE DESCRIPTION: SEQ ID NO:3:

Leu Lys Xaa His Ile Gly Pro Gly Arg Ala Phe Xaa
    1               5                   10

( 2 ) INFORMATION FOR SEQ ID NO:4:

( i ) SEQUENCE CHARACTERISTICS:
          ( A ) LENGTH: 12 amino acids
          ( B ) TYPE: amino acid
          ( D ) TOPOLOGY: both ( i i ) MOLECULE TYPE: peptide ( i i i ) HYPOTHETICAL: NO ( v ) FRAGMENT TYPE: internal ( i x ) FEATURE:
          ( A ) NAME/KEY: Modified-site
          ( B ) LOCATION: 1
          ( D ) OTHER INFORMATION: /label=Nle
                  / note="norleucine"

( i x ) FEATURE:
          ( A ) NAME/KEY: Modified-site
          ( B ) LOCATION: 3

-continued (D) OTHER INFORMATION: /label=Acap
/ note="6-aminocaproic acid"

(ix) FEATURE:
(A) NAME/KEY: Modified-site
(B) LOCATION: 12
(D) OTHER INFORMATION: /label=Acap
/ note="6-aminocaproic acid"

(ix) FEATURE:
(A) NAME/KEY: Cross-links
(B) LOCATION: 2..12
(D) OTHER INFORMATION: /label=cycle
/ note="amide through Lys alpha amino"

(xi) SEQUENCE DESCRIPTION: SEQ ID NO:4:

Leu Lys Xaa Gln Arg Gly Pro Gly Arg Ala Phe Xaa
1               5                   10